United States Patent
Demas et al.

(10) Patent No.: US 10,278,708 B2
(45) Date of Patent: May 7, 2019

(54) COMPRESSION DEVICE

(71) Applicant: Swift-Strap LLC, Cambridge, MA (US)

(72) Inventors: Nickolas Peter Demas, Manlius, NY (US); Anton Stuart Hunt, Houston, TX (US); Tyler T. Hamer, Cambridge, MA (US); Zaid Zayyad, Cambridge, MA (US); James F. Connor, Cambridge, MA (US); Julio C. Guerrero, Cambridge, MA (US); Pranay Jain, Delhi (IN)

(73) Assignee: SWIFT-STRAP LLC, Cambridge, MA (US)

( * ) Notice: Subject to any disclaimer, the term of this patent is extended or adjusted under 35 U.S.C. 154(b) by 203 days.

(21) Appl. No.: 15/116,488

(22) PCT Filed: Feb. 3, 2015

(86) PCT No.: PCT/US2015/014306
§ 371 (c)(1),
(2) Date: Aug. 3, 2016

(87) PCT Pub. No.: WO2015/119968
PCT Pub. Date: Aug. 13, 2015

(65) Prior Publication Data
US 2016/0345981 A1    Dec. 1, 2016

Related U.S. Application Data

(60) Provisional application No. 61/992,895, filed on May 14, 2014, provisional application No. 61/935,391, filed on Feb. 4, 2014.

(51) Int. Cl.
*A61B 17/132* (2006.01)

(52) U.S. Cl.
CPC ...... *A61B 17/1327* (2013.01); *A61B 17/1322* (2013.01)

(58) Field of Classification Search
CPC ............. Y10T 24/2192; Y10T 24/1418; Y10T 24/142; A61B 17/1322; A61B 17/1327
See application file for complete search history.

(56) References Cited

U.S. PATENT DOCUMENTS

| 1,447,967 A | 3/1923 | Davis |
| 2,113,534 A | 4/1938 | Brown |

(Continued)

FOREIGN PATENT DOCUMENTS

WO    2015119968 A1    8/2015

OTHER PUBLICATIONS

Written Opinion of the International Search Report for International Application No. PCT/US2015/014306 "Compression Device" dated Apr. 23, 2015.

(Continued)

*Primary Examiner* — Thomas M McEvoy
(74) *Attorney, Agent, or Firm* — Hamilton, Brook, Smith & Reynolds, P.C.

(57) ABSTRACT

A compression device, useful for applying circumferential compression to an object, for example, as a tourniquet to occlude blood flow in a hemorrhaging extremity, is provided. The device includes a buckle assembly, first and second guidance slides, a connecting member between the first and second guidance slides, and a strap. Each end of the strap is anchored to a guidance slide. From each of the anchored ends, the strap passes through the buckle assembly, forming outer segments. The strap then returns along respective insides of the outer segments and through the guidance slides, forming inner segments. The buckle assembly, inner segments and connecting member form a loop for placing (Continued)

about an object, an inner circumference of the loop being adjustable by pulling on a portion of the strap located along the outside of the connecting member and between the two guidance slides to tighten the loop around the object.

15 Claims, 22 Drawing Sheets

(56) References Cited

U.S. PATENT DOCUMENTS

| | | | |
|---|---|---|---|
| 2,754,825 A * | 7/1956 | Richmond | A61B 17/1327 606/203 |
| 6,217,601 B1 | 4/2001 | Chao | |
| 6,899,720 B1 | 5/2005 | McMillan | |
| 6,960,223 B1 | 11/2005 | Ambach | |
| 7,776,064 B2 | 8/2010 | Jennifer et al. | |
| 7,892,253 B2 | 2/2011 | Esposito et al. | |
| 8,343,182 B2 | 1/2013 | Kirkham | |
| 8,561,268 B2 | 10/2013 | Hortnagl | |
| 8,652,164 B1 | 2/2014 | Aston | |
| 2005/0049630 A1 * | 3/2005 | Ambach | A61B 17/1327 606/203 |
| 2005/0240217 A1 | 10/2005 | Jennifer | |
| 2009/0062842 A1 | 3/2009 | Esposito et al. | |
| 2010/0049241 A1 | 2/2010 | Persson | |
| 2010/0057120 A1 | 3/2010 | Kirkham | |
| 2012/0071917 A1 | 3/2012 | McDonald et al. | |
| 2015/0051638 A1 | 2/2015 | Dickinson et al. | |
| 2018/0042616 A1 | 2/2018 | Demas et al. | |

OTHER PUBLICATIONS

Written Opinion of the International Search Report for International Application No. PCT/US2016/022882 (Unpublished) "Compression Device" dated Jul. 13, 2016.
PCT/US2016/022882 (Unpublished) "Compression Device", Mar. 17, 2016.
Extended European Search Report for EP Application No. 16765747.7, entitled "Compression Device," dated: Dec. 10, 2018 (9 pgs).

* cited by examiner

COMPRESSION DEVICE

RELATED APPLICATIONS

This application is the U.S National Stage of International Application No. PCT/US2015/014306, filed on Feb. 3, 2015, which designates the U.S., published in English, and claims the benefit of U.S. Provisional Application Nos. 61/935,391, filed on Feb. 4, 2014, and 61/992,895, filed on May 14, 2014. The entire teachings of the above applications are incorporated herein by reference.

GOVERNMENT SUPPORT

This invention was made with government support under W81XWH-09-2-001 from USAMRMC. The government has certain rights in the invention.

BACKGROUND OF THE INVENTION

There are several tourniquets on the market that can be used, in cases of severe limb hemorrhage, by cinching to remove slack from the tourniquet and then tightening it to apply pressure to the limb. Many tourniquets have been made as devices that require two hands to effectively apply them, making them inappropriate for self-application. A few tourniquets that are applicable with just one hand, of the type described in U.S. Pat. Nos. 7,892,253 and 7,776,064, require pulling on webbing in a direction tangential to the limb for cinching. Pulling tangentially causes the tourniquet to rotate around the limb if adequate grip or frictional force is absent, which is usually the case when only one hand is used. This proves to be a hindrance in the cinching process, making the application of the tourniquet difficult and slow.

Many tourniquets have been made as devices that can be applied only on limbs with an accessible open end. These tourniquets are in the form of closed loops and can only be slid on from an open end, making them impossible to apply on entrapped or severely mangled limbs. A few tourniquets that are applicable on such limbs, of the type described in U.S. Pat. No. 8,343,182, are in the form of open loops that may be closed during application. However, accidental opening of the loop after application is a concern with these tourniquets.

U.S. Pat. No. 6,960,223 describes a tourniquet that may be applied with one hand and without pulling tangentially relative to the tourniquet. This tourniquet consists of two concentric loops formed such that pulling on the outer cinches the inner loop. However, pulling on the outer loop also creates friction between the loops, preventing the mechanism from effectively working U.S. Pat. No. 7,582,102 describes a tourniquet with a compliant support structure that provides friction between the limb and the device to prevent its rotation about the limb. However, this structure limits application to only limbs of certain sizes. It also adds bulk to the device making it difficult to carry. In addition, it has a tendency to severely pinch skin when applied. This can cause excessive pain and discomfort and prevent a user from adequately tightening the device, making it ineffective.

Most tourniquets produce a noticeable sound either during cinching, tightening or unpacking. Sound is particularly undesirable in military applications in hostile combat zones where it may expose the user's position.

SUMMARY OF THE INVENTION

The technique and designs of embodiments of this invention, on the other hand, readily and simply overcome limitations of prior approaches both in the area of tourniquets and in the more general areas of compression of objects and bundling and lifting objects. Embodiments involve the use of elongated members (e.g., straps) coupled with mechanisms and buckles in a way such that cinching and tightening operations happen on the same face of the device and require only one hand. Inner segments of the device are pulled through guidance slides, causing outer segments to pass through single-direction locking mechanisms and shorten in length. The inner and outer segments do not have notable friction buildup between one another during cinching. This allows for faster operation without excessive effort on the part of the user. The device may be opened and closed at will to position around a trapped limb. The mechanisms within the device achieve a single-direction locking action such that, once tight on an object, the device cannot open by mere accidental jerks or forces. This allows the tourniquet to be applied on trapped limbs without foregoing device safety. The device may be further tightened if needed via a tightening mechanism. The tightening mechanism has a grip for the operating hand and is easy, intuitive and fast to operate. All mechanisms and packaging are such that they make minimal noise and are hence safe to use in hostile combat zones.

A device that applies circumferential pressure on objects to which it is applied may comprise members with mechanisms and buckles that are used to secure it around an object and tighten it sufficiently. Procedures to secure and tighten may be performed on the same face or side of the device. This makes it easier and faster to apply for the user. In an embodiment, the device may act as a tourniquet and provide pressure sufficient to occlude blood flow when applied on a limb. The device may be applied with only one hand and on limbs without any accessible open end.

The device may be an assembly of flexible elongated members, buckles and a tightening mechanism. A first flexible elongated member, e.g., a strap made from webbing, is routed through a pair of mating buckles. The mating buckles are such that they allow an elongated member to be drawn in only one direction along its length. The tightening mechanism, e.g., a windlass system, is attached to a flexible second elongated member. A second elongated member is attached to the first elongated member directly or indirectly, e.g., through guidance slides. The device can be kept together with sacrificial attachments that keep the device in its initial shape before deployment and come apart or scrunch up when the device is used.

When applied on an object, the device is placed around the object. This can be done by sliding the device onto the object or separating a first buckle assembly, placing the device around the object, and finally reconnecting the first buckle assembly. The portion of the first elongated member that is routed on top of the tightening mechanism is pulled away from the object. This motion cinches the loop down onto the object, removing all slack from the loop and applying circumferential pressure to the object. The mechanisms in the first buckle assembly prohibit the first elongated member from loosening. Required action on the tightening mechanism may be performed to induce further necessary circumferential pressure.

A compression device includes a buckle assembly having first and second buckles, a first guidance slide, a second guidance slide, a connecting member between the first and second guidance slides, and a strap having a first end and a second end. The first end of the strap is anchored to the first guidance slide and the second end of the strap is anchored to the second guidance slide. The strap passes from the first guidance slide through the first buckle, forming a first outer segment. The strap returns from the first buckle on an inside of the first outer segment and through the first guidance slide, forming a first inner segment. From the first guidance slide, the strap passes on an outside of the connecting member to the second guidance slide. The strap passes through the second guidance slide and through the second buckle, forming a second inner segment. The strap returns from the second buckle on an outside of the second inner segment to the second guidance slide, forming a second outer segment. The buckle assembly, inner segments and connecting member form a loop for placing about an object, an inner circumference of the loop being adjustable by pulling on a portion of the strap located along the outside of the connecting member and between the two guidance slides to tighten the loop around the object.

The compression device can further include a tightening mechanism between the first and second guidance slides to further tighten the loop around the object. The tightening mechanism may be a windlass that includes a windlass strap connected to the connecting member between the first and second guidance slides, and that further includes a windlass stick defining a slot through which the windlass strip passes. The windlass stick can have a shape having a wide top portion for grasping and a narrow bottom portion having the slot through which the windlass strip passes. The windlass stick may have a trapezoidal shape, and it may include one or more openings. The compression device can further include a locking mechanism to lock the windlass in place. The locking device can include one or more carabiner clasps to engage an opening in the windlass stick.

The strap of the compression device can be webbing, and it can be about 1.5 inches wide. The compression device can further include a second buckle assembly to separate the strap into two parts. The second buckle assembly can be connected in-line with the portion of the strap located along the outside of the connecting member and between the two guidance slides.

The buckle assembly can include a popper assembly that releasingly connects the first and second buckles. The popper assembly can include at least one male popper riveted to a first short flexible member and at least one female popper riveted to a second short flexible member, the flexible members attached to the buckle assembly. Each buckle can include a rigid projection configured to prevent rotation of the buckle relative to the buckle assembly. The buckle assembly can include buckles with single direction locking mechanisms.

A method of compressing an object includes placing a loop about an object and tightening the loop. The loop is formed from a strap, a buckle assembly, and a connecting member. The strap has two outer segments, two inner segments, and a portion located along the outside of the connecting member. The outer and inner segments are joined at the buckle assembly. The loop is tightened by pulling on the portion of the strap located along the outside of the connecting member and causing the inner and outer segments to shorten in length. The inner segments pass through guidance slides on an inside of the outer segments.

The method can further include twisting a windlass stick having a windlass strap threaded therethrough to further tighten the loop around the object, the windlass strap being connected to the connecting member. The method can further include securing the windlass stick to a locking mechanism. Placing the loop can include unjoining the inner and outer sections of the strap at the buckle assembly, wrapping the loop about the object, and rejoining the segments at the buckle assembly. This unjoining and rejoining may be performed using a popper assembly. The placing and tightening of the loop may be performed using a single hand. The loop can be maintained in a tightened position using two buckles, each having a single direction locking mechanism.

A windlass device includes a windlass strap, a windlass stick, and a locking mechanism. The windlass stick has a wide top portion for grasping and a narrow bottom portion having a first opening through which the windlass strap passes. The locking mechanism engages a second opening in the windlass stick and locks the windlass stick in place. The windlass stick may have a trapezoidal shape. The locking mechanism can include a carabiner clip.

Embodiments of the present invention have many advantages. The compression device and method are useful for applying pressure on a limb in a manner suitable for the occlusion of blood flow. The device can be used as a tourniquet in military and civilian settings. The tourniquet can be applied with one hand and around objects or limbs with no accessible open end. Additionally, the tourniquet does not normally slip or rotate during application and it does not pinch skin or other loose objects or surfaces during application. Minimal noise is made during the application and tightening of the device. The device is lightweight and compact so as to be easy to carry and quick to deploy.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

The teachings of all patents, published applications and references cited herein are incorporated by reference in their entirety.

Figure 1:
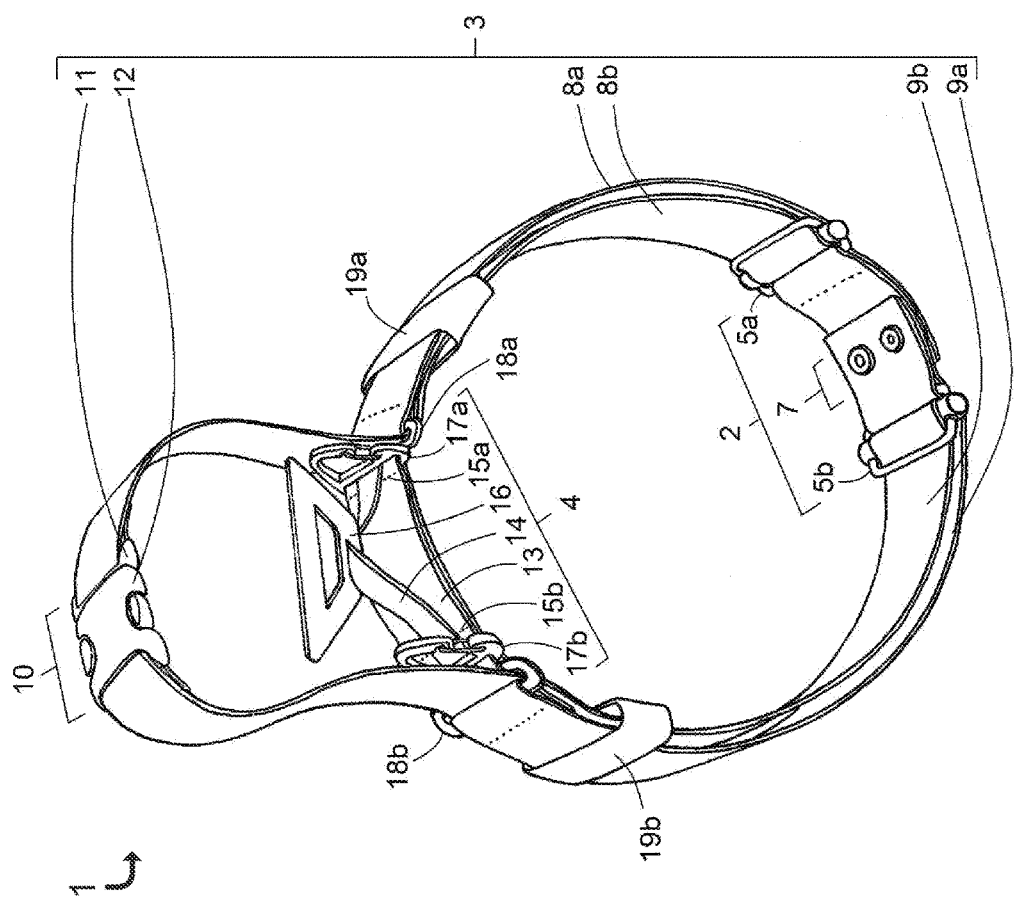
FIG. 1 is an isometric view of a compression device in accordance with an embodiment of the present invention shown in a relaxed state, ready for application.
Figure 2:
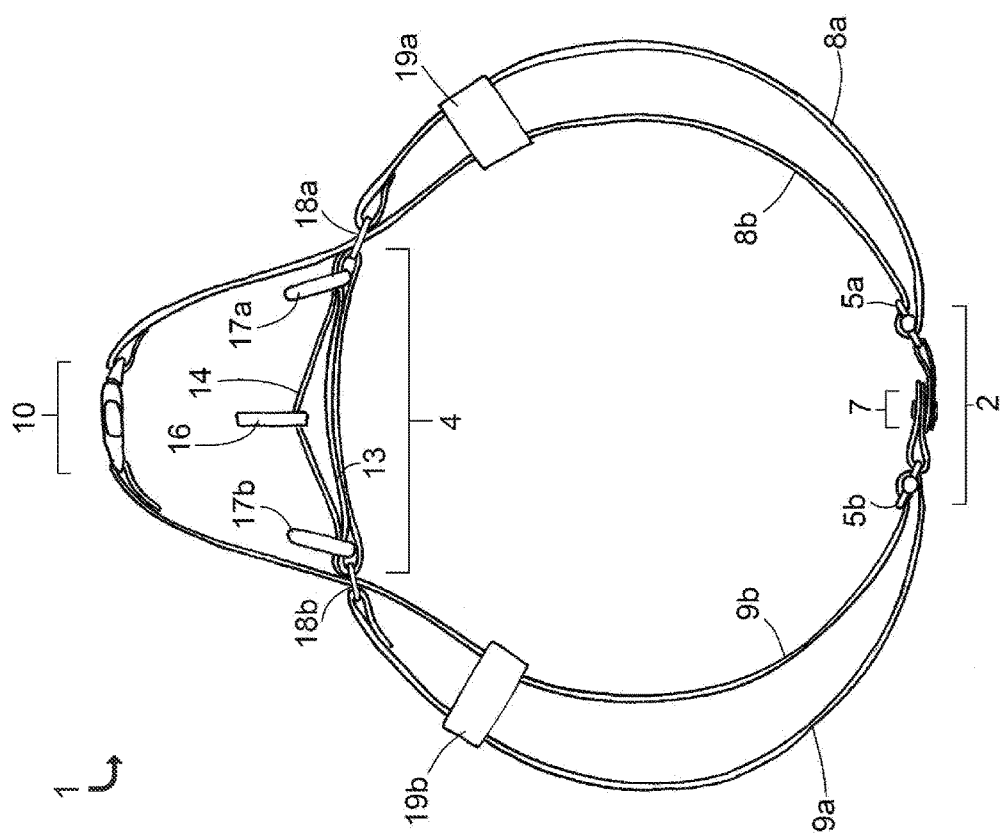
FIG. 2 is a side view of the device shown in FIG. 1.

Referring to FIGS. 1-2, a compression device 1 according to an embodiment of the present invention is shown. The compression device 1, as shown, is a tourniquet. The device includes a first buckle assembly 2, a cinch member (strap) 3, and a tightening mechanism 4. The first buckle assembly 2 includes sliding buckles 5a and 5b, both of which have sliding bars 6a and 6b designed to accomplish a single-direction locking action further described with reference to FIGS. 10-13. The first buckle assembly 2 can be joined/separated using the popper assembly 7. The cinch member 3 comprises a first flexible elongated member, including outer segment 8a and inner segment 8b, outer segment 9a and inner segment 9b, and an optional second buckle assembly 10. The second buckle assembly 10 includes a second male buckle 11 and a second female buckle 12. The compression device further includes a first guidance slide 18a, a second guidance slide 18b, sacrificial attachments 19a and 19b, and anchor points illustrated by dashed lines. A second elongated member connects guidance slides 18a and 18b. The tightening mechanism 4 includes a third elongated member 14 fixed at two anchor points 15a and 15b, a windlass stick 16 and carabiner clasps 17a and 17b.

Referring again to FIGS. 1-2, the construction of the tourniquet 1 is as follows. Inner segment 8b of cinch member 3 is fixed with an anchor point to the second male buckle 11. Anchor points (dashed lines) can be fixed using, for example but not restricted to, sewing, gluing, stapling, clamping, heat/ultra-sound (sonic) welding, or any combinations thereof. Inner segment 8b of cinch member 3 is brought through the first guidance slide 18a and fed through the sliding buckle 5a. Outer segment 8a of cinch member 3 returns from sliding buckle 5a along an outside of inner segment 8b and is fixed to the guidance slide 18a with an anchor point. Similarly, inner segment 9b of cinch member 3 is fixed with an anchor point to the second female buckle 12. Inner segment 9b of cinch member 3 is brought through the second guidance slide 18b and fed through sliding buckle 5b. Outer segment 9a of cinch member 3 returns from sliding buckle 5b along an outside of inner segment 9b and is fixed to guidance slide 18b with an anchor point. The second male buckle 11 and the second female buckle 12 are connected, forming the second buckle assembly 10. The sliding buckles 5a and 5b are connected using the popper assembly 7, forming the first buckle assembly 2.

In an embodiment the second buckle assembly 10 can be substituted with a popper assembly, similar to popper assembly 7. Alternatively, the second buckle assembly 10 may be omitted, such that cinch member 3 is a single strap forming outer segments 8a, 9a and inner segments 9a, 9b.

Figure 3:
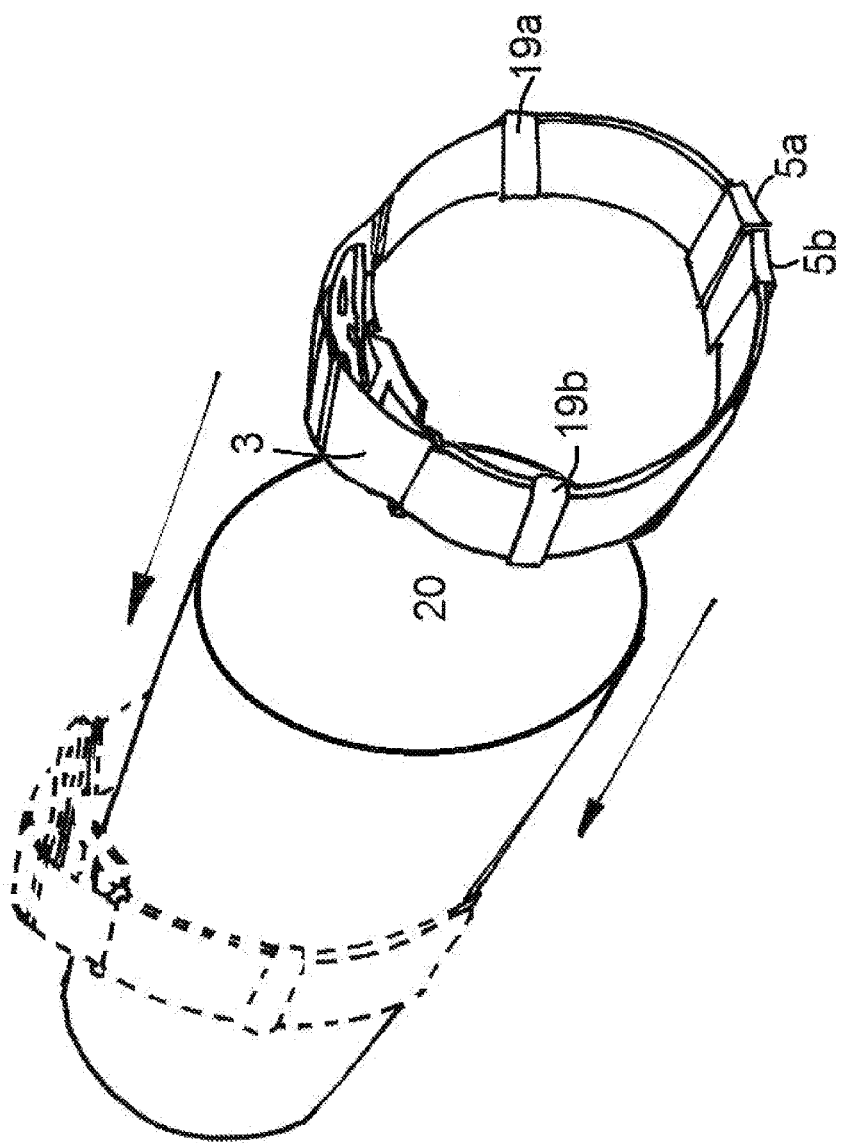
FIG. 3 illustrates the application of a compression device on a limb, of which only a representative portion is shown, by sliding the device in from the accessible open end of the limb.

Referring again to FIGS. 1-2, a tightening mechanism 4 includes a windlass, a mechanism whereby twisting a flexible member causes the flexible member to shorten in length. A second elongated member 13 is fixed between guidance slides 18a and 18b using anchor points 15a and 15b respectively. A third elongated member 14 passes through a windlass stick 16 and the third elongated member 14 is fastened to the second elongated member 13 at anchor points 15a and 15b, after passing through guidance slides 18a and 18b. Sacrificial attachments 19a and 19b are loops that may be included to keep bundled the layers formed by the first elongated member, including outer segment 8a and inner segment 8b, and outer segment 9a and inner segment 9b. These sacrificial attachments could be made of, for example but not restricted to, glue, paper, plastic, thread, Velcro® backed fabric, magnetically latched strips, or some combination thereof. The sacrificial attachments 19a and 19b ensure that there is only one obvious large open loop in which a bleeding limb 20 may be placed into the tourniquet 1, as shown in FIG. 3. The sacrificial attachments 19a and 19b can be one-time use and can come apart or scrunch up when the user affects the cinch member 3. Alternatively, the sacrificial attachments 19a and 19b could be reset and used again, or removed entirely.

Each elongated member may alternatively be referred to as a strap. All straps, or portions of each strap, can be made of webbing. Cinch member 3 and second elongated member 13 may be straps having a width of approximately 1.5 inches. Third elongated member 14 may be a strap having a narrower width than the width of second elongated member 13.

Figure 4:
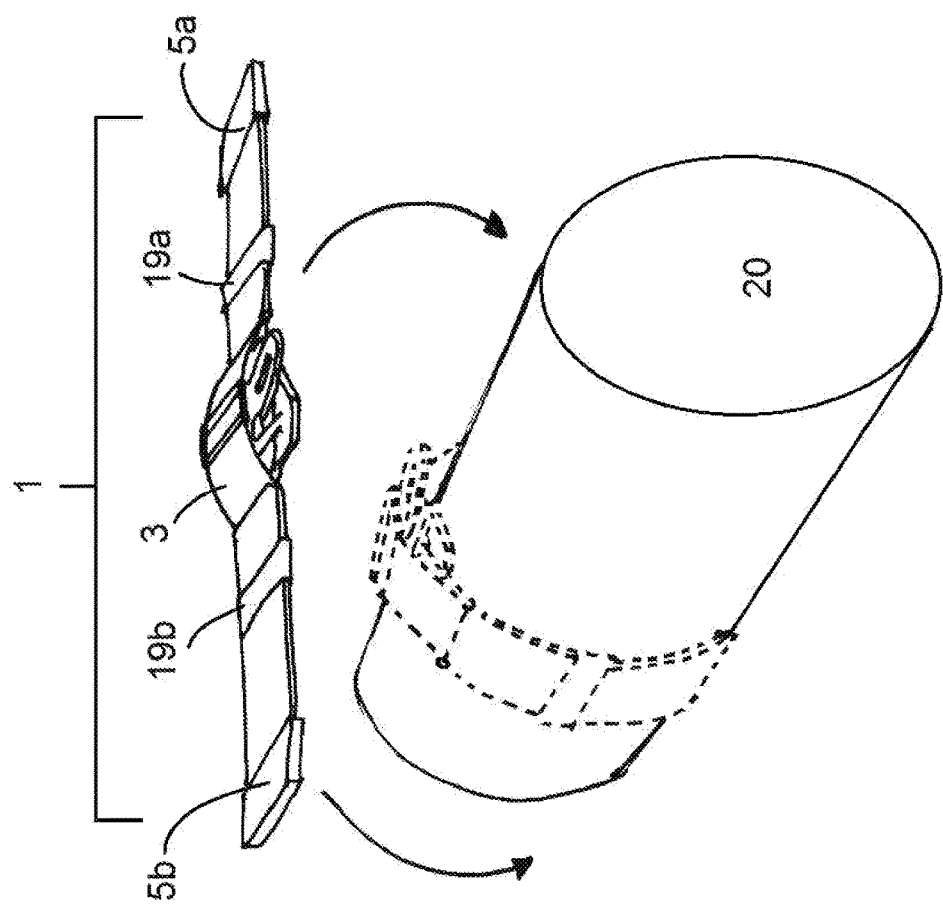
FIG. 4 illustrates the application of a compression device in FIG. 1 on a limb, of which only a representative portion is shown, by disconnecting and reconnecting a first buckle assembly of the device around the limb.
Figure 5:
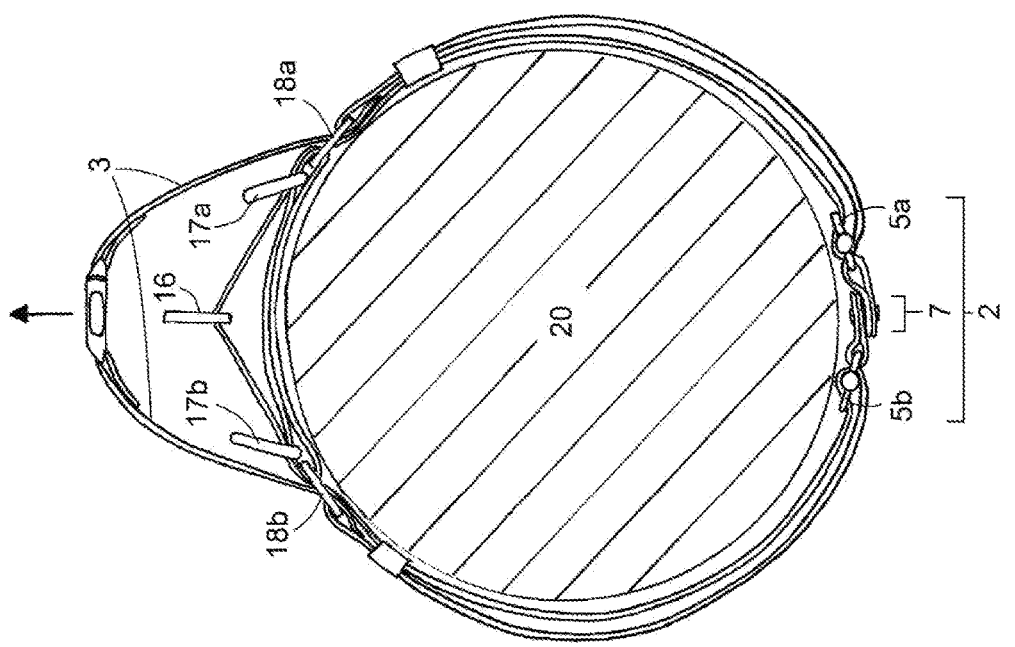
FIG. 5 is a side view illustrating cinching of the device of FIG. 1 over the limb, which is sectioned in the plane of viewing.

Referring to FIGS. 3-5, self-application of the tourniquet 1 is illustrated. As a first step, a person (not shown) places the tourniquet 1 circumferentially around the bleeding limb 20. If the path to the limb is free, the person can slip the tourniquet 1 over the limb 20 and move the tourniquet 1 into a position proximal to the location of an injury, as shown in FIG. 3. If the path is blocked and the tourniquet 1 cannot be positioned by threading the bleeding limb 20 through the tourniquet 1, which may be the case if the limb is trapped or badly mangled, the sliding buckles 5a and 5b can be disconnected through the popper assembly 7 and reconnected around the bleeding limb 20, as shown in FIG. 4. The tourniquet 1, regardless of being slipped on or clipped on, would now loosely circumscribe the limb 20. As a second step, the person can then pull the portion of cinch member 3 located between guidance slides 18*a* and 18*b* in a direction away from windlass stick 16, as shown in FIG. 5. The pulling action cinches the tourniquet against the bleeding limb 20 and breaks the sacrificial attachments 19*a* and 19*b* if they are present. Sliding buckles 5*a* and 5*b*, further described with reference to FIG. 10, maintain the compression applied to bleeding limb 20 caused by the pulling of cinch member 3 and do not allow the tourniquet to loosen once the person lets go of cinch member 3.

In the case of self-application, the tourniquet 1 may be positioned such that the person can cinch the tourniquet by pulling on the portion of cinch member 3 located between guidance slides 18*a* and 18*b* in a direction toward him/herself, allowing for easy application.

Figure 6:
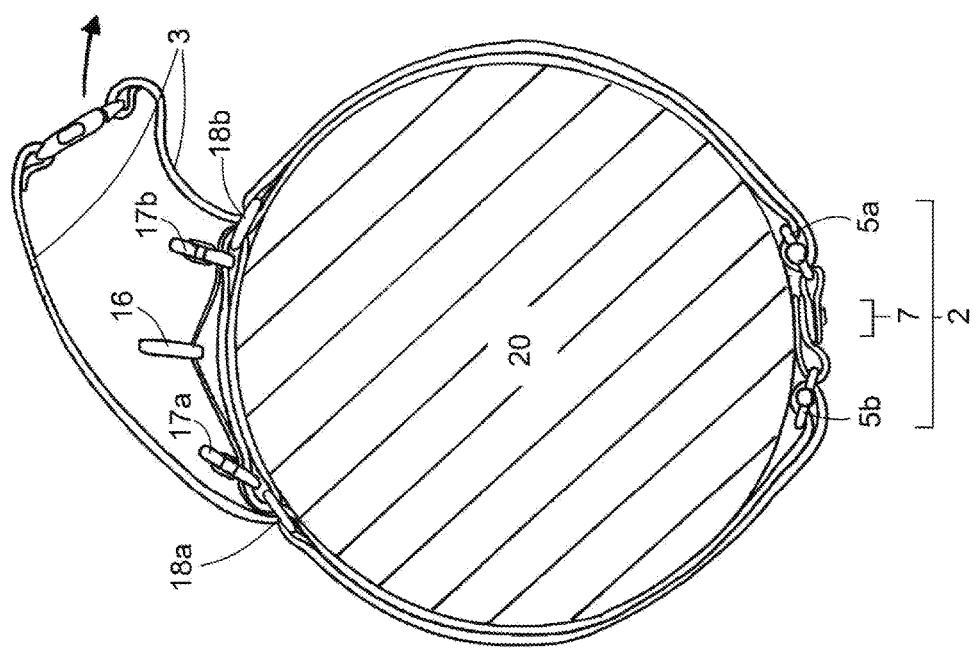
FIG. 6 is a side view illustrating further cinching of the device of FIG. 5.

Referring to FIG. 6, additional compression can be attained by pulling tangentially on the cinch member 3 in one or both directions away from windlass stick 16. The friction forces generated between the elongated members after the initial cinch step are enough to stop the tourniquet 1 from rotating during the tangential pull.

Figure 7:
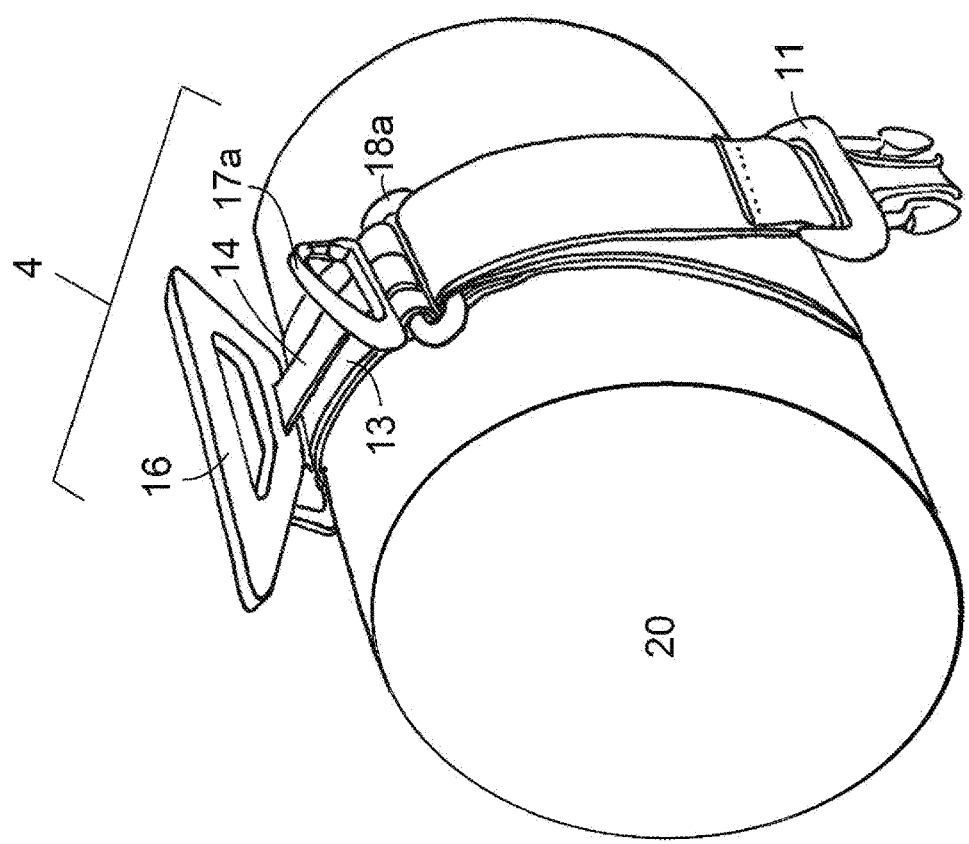
FIG. 7 is a perspective view of the device in FIG. 1 cinched over a limb, of which only a representative portion is shown, with the vicinity of the tightening mechanism cleared of the cinch member.

Referring to FIG. 7, following cinching, the second male buckle 11 can then be disconnected from the second female buckle 12 (not shown in FIG. 7), so that the loop formed by the portion of cinch member 3 located between guidance slides 18*a* and 18*b* can be cleared from the vicinity of the tightening mechanism 4.

Figure 8:
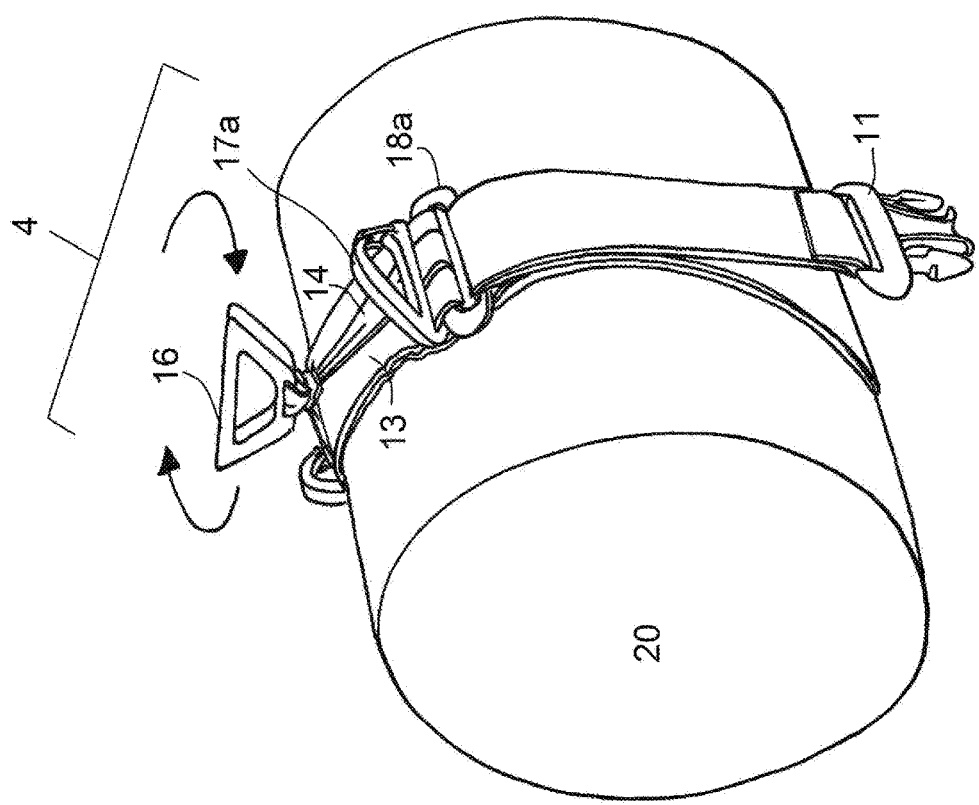
FIG. 8 is a perspective view of the device in FIG. 7 being tightened over a limb, of which only a representative portion is shown, by twisting of the windlass stick.

Referring to FIG. 8, the tightening mechanism 4 faces in the same direction as that of which cinch member 3 was pulled, which, for self-application, will be facing the user. The user then rotates the windlass stick 16 in either a clockwise or counterclockwise motion, causing the third elongated member 14 to wrap into a helix and reduce the overall length between guidance buckles 18*a* and 18*b*. Decreasing this length increases compressive force exerted into the bleeding limb 20 by the tourniquet 1. The windlass stick 16 can be tightened until blood flow is occluded. The windlass stick 16 can then be secured in either carabiner clasp 17*a* or 17*b*. A one-way spring gate of the carabiner clasp prohibits the release of windlass stick 16 thereby prohibiting the third elongated member 14 from unwinding and preventing accidental slackening of the tourniquet 1.

Figure 9:
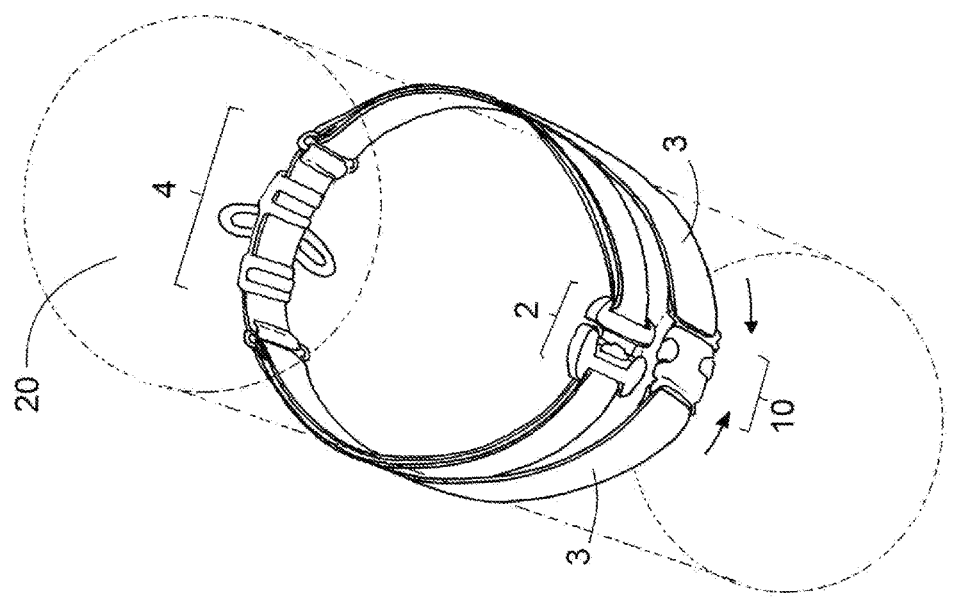
FIG. 9 is a perspective view of a compression device illustrating the optional connection of the second male and female buckles on the opposite side after cinching.

Referring to FIG. 9, the loose second male buckle 11 and second female buckle 12 can then be attached on the opposite side of the limb if it is accessible and if there exists enough slack in the cinch member 3. The ends could be left to dangle as shown in FIG. 8 if there is not enough slack in cinch member 3. To remove the tourniquet 1 from the bleeding limb 20, the first elongated member, including outer segments 8*a* and 9*a* and inner segments 8*b* and 9*b*, or the second elongated member 13 and third elongated member 14 can be cut using a surgical scissors. Alternatively, the tourniquet 1 could also be removed by separating the sliding buckles 5*a* and 5*b* by means of the popper assembly 7.

The compression device described herein includes features that improve the ease and speed of application over prior art devices. A prior approach described in U.S. Pat. No. 6,960,223 B1, requires the user to pull on a cord located about an outer periphery of the device, causing friction to build up during application of the device and preventing easy tightening about a limb. Additionally, the prior approach locates a lever for further tightening on an opposite side of the device, relative to the side from which the cord is pulled. This makes it difficult for the user to access the lever, especially in cases of self-application.

Embodiments of the present invention include a first elongated member, or strap, which, when pulled, applies tension to inner segments of the tourniquet during cinching. This avoids friction buildup between inner and outer segments of the tourniquet during cinching and also prevents skin pinching.

Embodiments of the present invention use single direction locking mechanisms to allow the strap to be cinched easily with one hand and to maintain circumferential pressure to the bleeding limb 20 even after tension has been removed from the cinch member 3 by the user. The operation of this mechanism is also silent, which is useful in hostile combat zones for a tourniquet.

Prior art approaches, such as described in U.S. Pat. No. 7,892,253 B2, utilize a Velcro®-like strap running through a buckle design, which is difficult to tighten securely with one hand and which creates significant noise when cinched. In addition, there is a risk that the Velcro® running through the buckle catches on itself, particularly at the location of the buckle.

Embodiments of the present invention, such as tourniquet 1, have a first buckle assembly 2 which cannot be easily released when the first buckle assembly 2 is under tension. This can reduce or eliminate the risk that the occlusion of the limb, from application of the tourniquet, is lost due to the buckle being accidentally released. In contrast, the device described in U.S. Pat. No. 7,582,102 B2 includes a quick release button that can be accidentally actuated if the device is rolled over or struck with an object.

Figure 10:
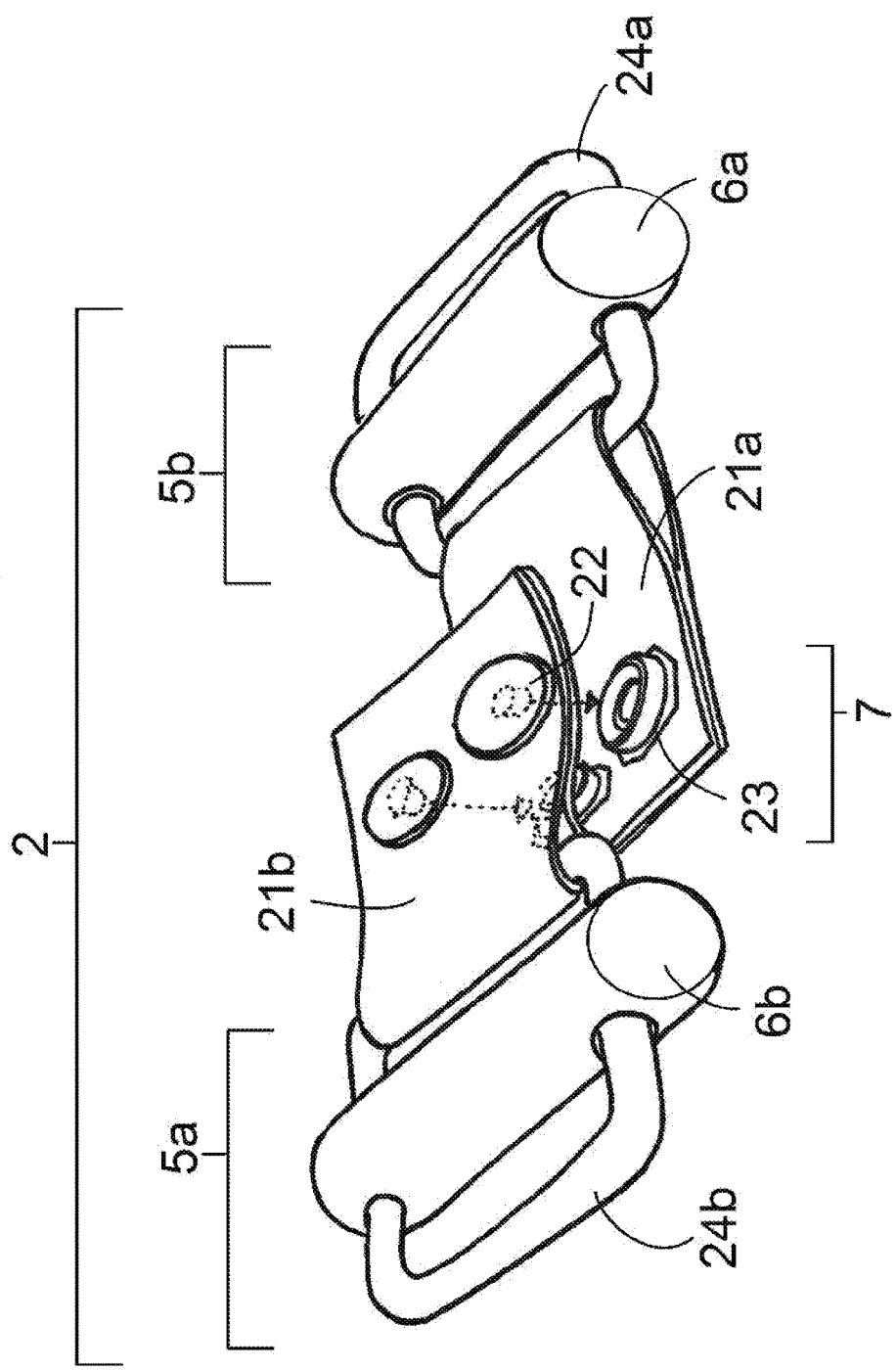
FIG. 10 is an isometric view of the first buckle assembly illustrating how the sliding buckles can be connected together using poppers.

Referring to FIG. 10, a perspective view of the first buckle assembly 2 is shown, including sliding buckles 5*a* and 5*b*. Sliding buckles 5*a* and 5*b* are connected by means of a popper assembly 7, with a male popper 22 and a female popper 23. Short flexible members 21*a* and 21*b*, anchored to sliding buckles 5*a* and 5*b* through popper assembly 7 respectively, provide the attachment points for popper assembly 7. The pair of male poppers 22 are riveted to short flexible member 21*a* and the pair of female poppers 23 are riveted to short flexible member 21*b*. The sliding buckles 5*a* and 5*b* have a single-direction locking mechanism including sliding bars 6*a* and 6*b* and static wireform loops 24*a* and 24*b*. The strap, or first elongated member, is routed through each sliding buckle. Outer segment 8*a* and inner segment 8*b* are routed through sliding buckle 5*a*, and outer segment 9*a* and inner segment 9*b* are routed through sliding buckle 5*b*, as shown in FIGS. 1-2.

Figure 11:
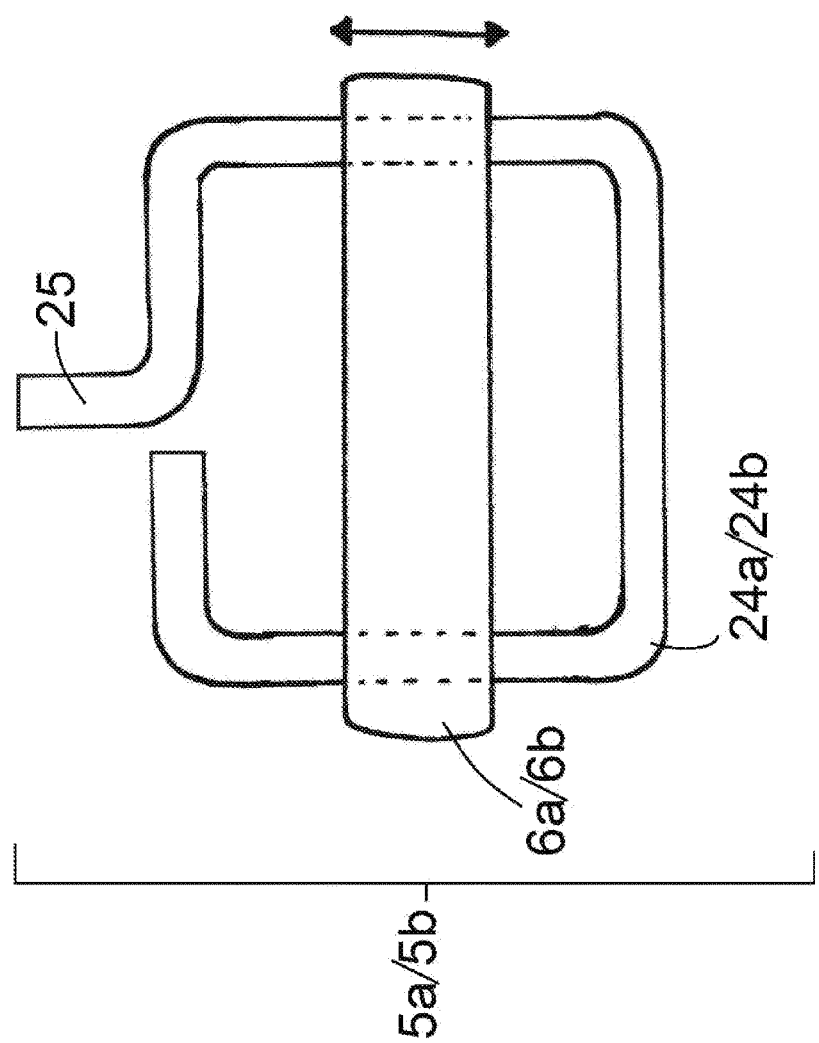
FIG. 11 is a plan view of a single direction locking mechanism of the sliding buckles shown in FIG. 10.

Referring to FIG. 11, a top view of the sliding buckle 5*a* or 5*b* is shown, illustrating the degree of freedom of the sliding bar 6*a* or 6*b*. The sliding bars 6*a*, 6*b* can press up against segments of the wireform loops 24*a*, 24*b*. Feature 25, a rigid projection, is included in both static wireform loops 24*a* and 24*b* and runs inside short flexible members 21*a* and 21*b*. Feature 25 ensures that the second buckle assembly 2 cannot rotate on itself under normal operation.

Figure 12:
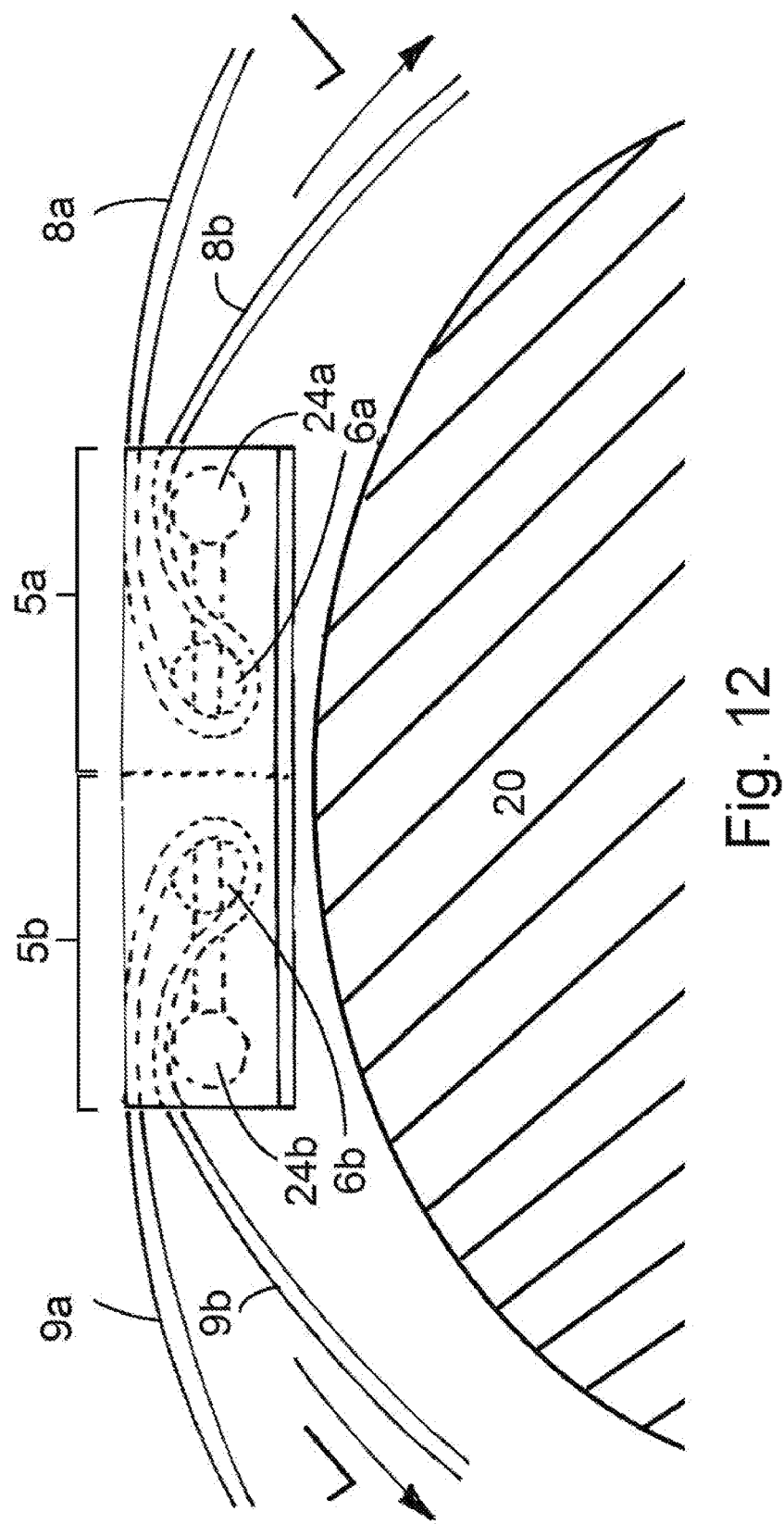
FIG. 12 is a schematic side view of sliding buckles with an elongated member passing through each, illustrating the allowed direction of motion.

Referring to FIG. 12, a configuration of the strap with sliding buckles 5*a*, 5*b* is shown. The first elongated member (strap) is fed through sliding buckle 5*b*, around sliding bar 6*b*, and over static wireform loop 24*b*, defining the transition of the strap from outer segment 9*a* to inner segment 9*b*. The first elongated member is similarly fed through sliding buckle 5*a*, around sliding bar 6*a*, and over static wireform loop 24*a*, defining the transition of the strap outer segment 8*a* to inner segment 8*b*. The first elongated member is free to move when pulled from inner segments 8*b*, 9*b* (in the directions marked with arrows in FIG. 12). During active pulling of cinch member 3 (shown in FIG. 5), the tension applied to inner segments 8*b*, 9*b* causes the sliding bars 6*a*, 6*b* to be pushed away from the static wireform loops 24*a*, 24*b*, permitting the strap to move with little frictional resistance. Sliding buckles 5*a*, 5*b* may be enclosed in respective housings (as indicated by solid lines in FIGS. 12-13). Sliding buckles 5a, 5b and their respective housings may be separable (as indicated by the vertical dashed line in FIGS. 12-13).

Figure 13:
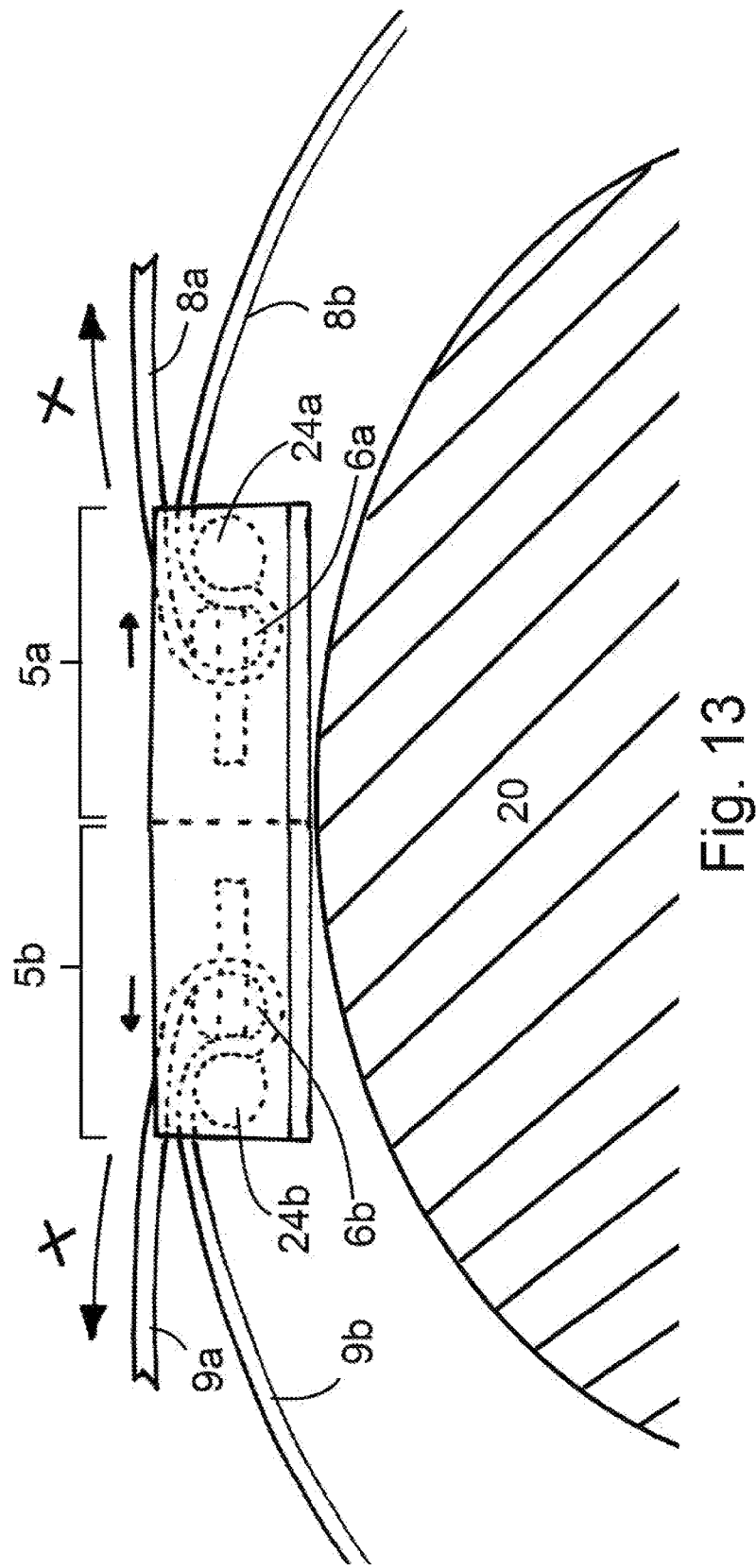
FIG. 13 is a schematic side view of the sliding buckles in FIG. 12 with an elongated member passing through them, illustrating the restricted direction of motion.

Referring to FIG. 13, the clamped positions of the sliding bars 6a and 6b relative to the static wireform loops 24a and 24b are shown when an attempt to pull the outer segments 8a or 9a is made (in the directions marked with arrows in FIG. 13). The strap experiences a large frictional resistance via the capstan effect. The pulling of cinch member 3 causes the sliding bars 6a, 6b to be pulled toward the static wireform loops 24a, 24b, which, in turn, causes the strap to become pinched between these features, creating a locking effect. This prevents the strap from loosening once cinch member 3 is released by the user. The surface finish of the sliding bars 6a and 6b and/or the static wireform loops 24a and 24b can be smooth for ease of manufacturing, but ribbing, texture, interlocking features or other surface elements could be added to provide additional gripping force.

The first elongated member is therefore free to move when pulled from inner segments 8b, 9b, but rapidly jams and lodges in place when pulled from outer segments 8a, 9a. This permits the tourniquet 1 to be tightened about the bleeding limb 20 by pulling on cinch member 3 and causing the inner segments 8b, 9b and outer segments 8a, 9a to shorten in length without frictional interference, or at least without an amount of frictional interference that is significant enough to impede application of the tourniquet 1. However, after tightening about the limb 20, the inner segments 8b, 9b and outer segments 8a, 9a of the tourniquet 1 remain locked in position. The sliding buckles 5a, 5b thus accomplish a single-direction locking action.

Figure 14:
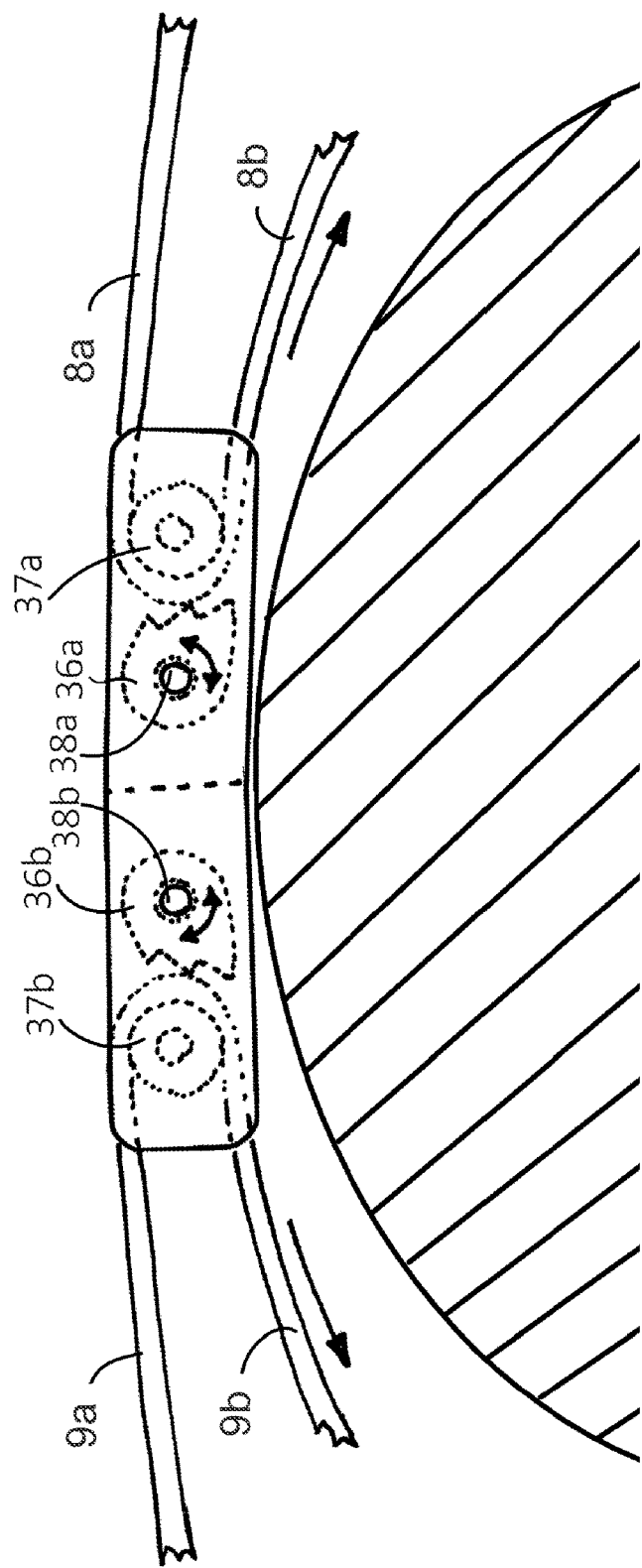
FIG. 14 is a schematic side view illustrating an alternative embodiment of the internal structure of the first buckle assembly utilizing a rotational cam cleat.
Figure 15:
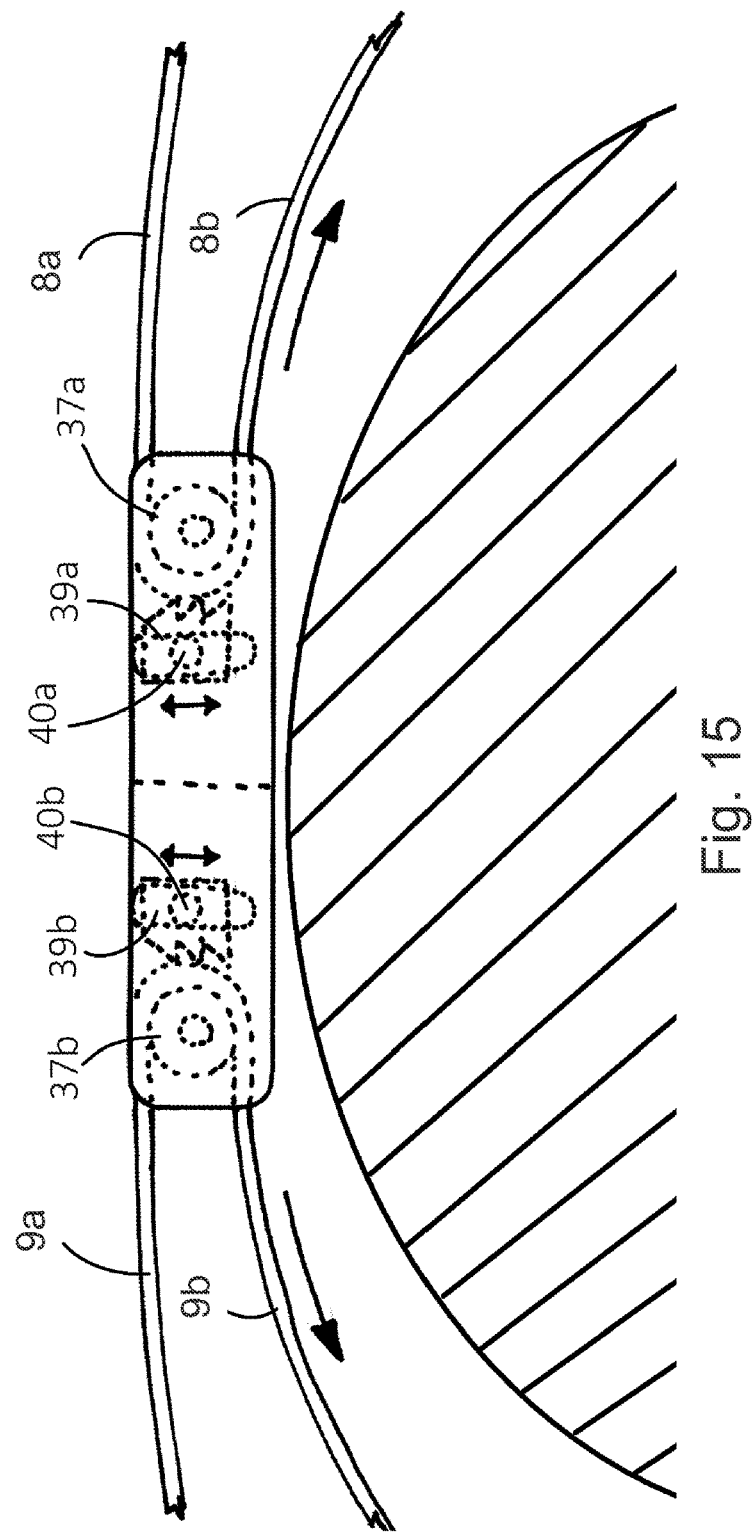
FIG. 15 is a schematic side view illustrating yet another alternative embodiment of the internal structure of the first buckle assembly utilizing a linear cam cleat.
Figure 16:
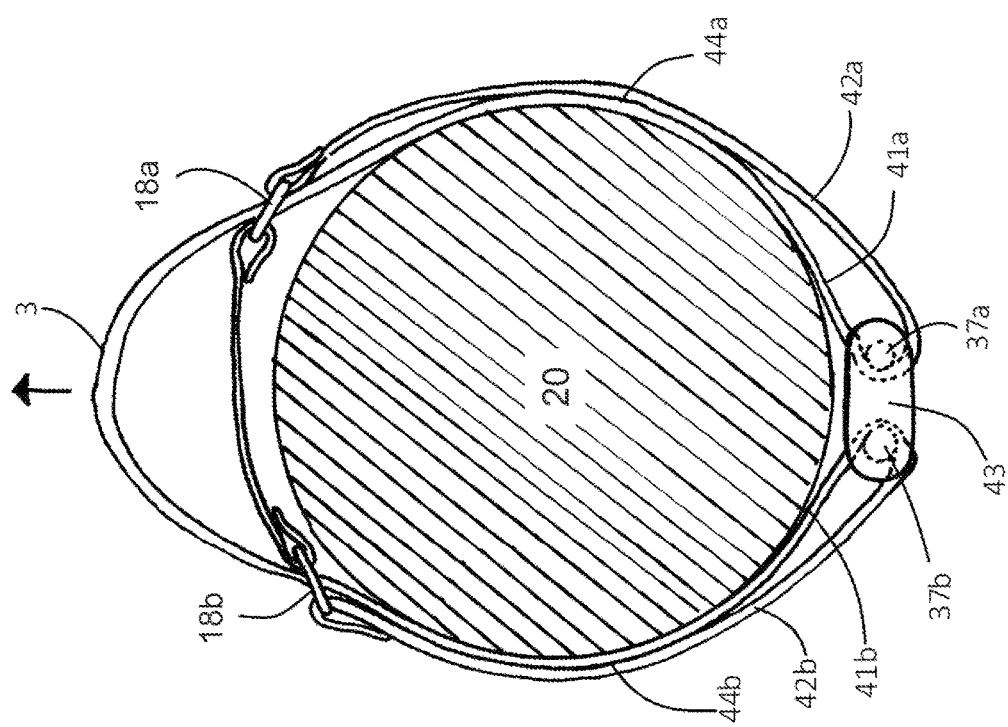
FIG. 16 is a side view illustrating an embodiment of a compression device that relies on friction between the bands for the single direction locking action over the limb, which is sectioned in the plane of viewing.

Alternative embodiments of single-direction locking action by a buckle assembly are shown in FIGS. 14-16.

Referring to FIG. 14, an embodiment of the single-direction locking action is accomplished with rotational cam cleats 36a and 36b. The rotational cam cleats 36a, 36b jam and lock the strap against static shafts 37a and 37b. The rotational cam cleats 36a, 36b rotate about pivot pins 38a and 38b, and are held pressed against the strap by a spring to apply torsion. The gripping elements of the rotational cam cleats 36a, 36b have a profile such that they accomplish the single-direction locking of the strap, permitting movement of the strap when the strap is pulled from inner segments 8b, 9b and prohibiting movement of the strap when the strap is pulled from outer segments 8a, 9a.

Referring to FIG. 15, an embodiment of the single-direction locking action is accomplished with linear cam cleats 39a and 39b. The linear cam cleats 39a, 39b jam and lock the strap up against static shafts 37a and 37b. The linear cam cleats 39a, 39b are guided by slot-and-pin arrangements 40a and 40b. The linear cam cleats 39a, 39b are wedges with a restorative spring force maintaining contact between the linear cam cleats 39a, 39b, the strap, and the static shafts 37a, 37b. The gripping elements of the linear cam cleats 39a, 39b have a profile such that they accomplish single-direction locking of the strap in a similar manner as described above.

Referring to FIG. 16, an embodiment of the single direction locking action is accomplished with passive frictional force between inner portions 41a, 41b and outer portions 42a, 42b of the cinch member (strap) 3. This passive frictional force maintains circumferential pressure after the device has been cinched and tension on the cinch member 3 has been removed. A holding structure 43 supporting two static shafts 37a and 37b is shown. The strap is routed over the two static shafts 37a, 37b, defining inner portions 41a, 41b and outer portions 42a, 42b of the cinch member 3. The inner portions 41a, 41b are pulled (in the direction indicated by the arrow), causing both inner portions 41a, 41b and outer portions 42a, 42b to shorten and cinch a limb or object. Guidance slides 18a and 18b are used to route inner portions 41a, 41b during cinching. Due to this configuration, the inner and outer segments do not have notable friction buildup between one another during the process of cinching. A locking action is accomplished following cinching, when the device is tightened about an object, by friction interfaces 44a and 44b between the inner portions 41a, 41b and the outer portions 42a, 42b of cinch member 3.

Figure 17:
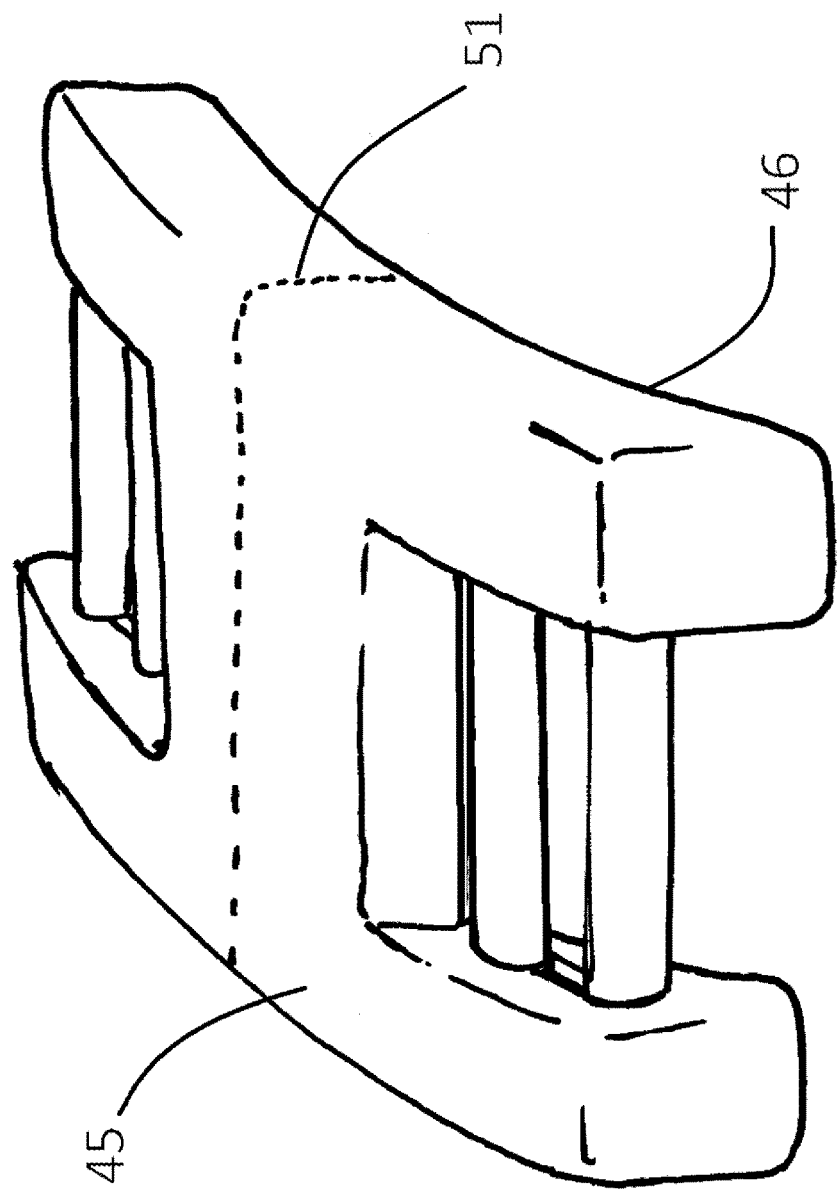
FIG. 17 is a perspective view of a buckle assembly for use with embodiments of the invention.

An alternative embodiment of a first buckle assembly is shown in FIG. 17. A first buckle assembly 2 includes a single, inseparable unit 45. A conforming surface 46 is shaped to conform or interface with an object or limb, improving pressure distribution and ease of application of a compression device. The first buckle assembly 2 may further include an adjustable hinge 51 to more closely conform the buckle assembly 2 about objects or limbs of various sizes.

Figure 18:
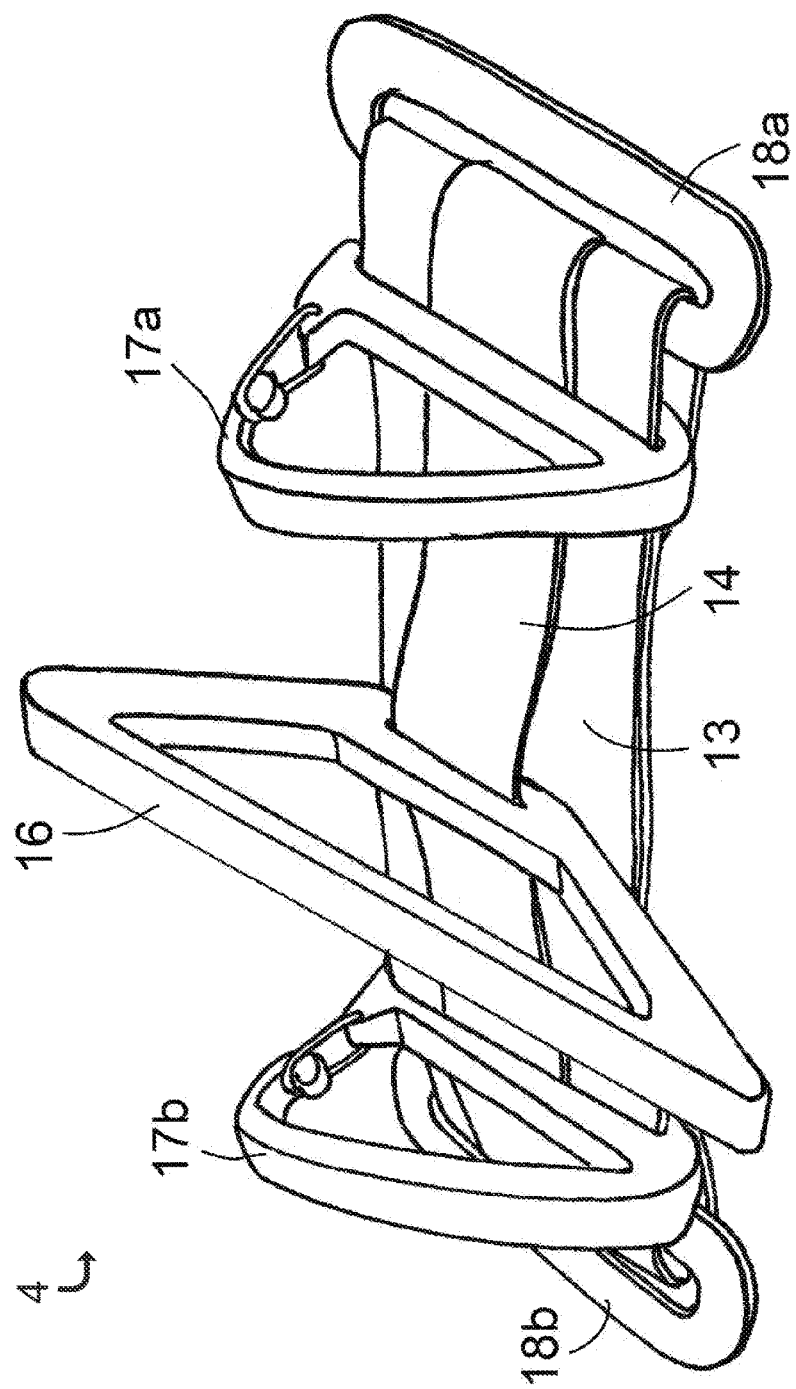
FIG. 18 is a perspective view of the tightening mechanism of the device in FIG. 1.

Referring to FIG. 18, the construction of the tightening mechanism 4 of FIG. 1 is shown. The tightening mechanism 4 includes a windlass stick 16 with the third elongated member 14 passing through a slot located in a lower portion of the windlass stick 16. Twisting of the windlass stick 16 results in the formation of a helix of the third elongated member 14, drawing the ends of the third elongated member 14 and guidance slides 18a, 18b in towards the center of rotation at the base of the windlass stick 16 (shown in FIG. 8). A large tensile force is consequently generated through this twisting motion of the windlass stick 16 in the third elongated member 14, further compressing an object or limb circumscribed by the compression device 1. Once sufficient compression is realized by an adequate number of rotations of the windlass stick 16, the windlass stick 16 can be locked in position using carabiner clasps 17a or 17b, preventing the helix from unwinding and maintaining pressure on the object or limb. The compressive force can be decreased in a controlled manner by releasing the windlass stick 16 from the carabiner clasp 17a or 17b and slowly rotating the windlass stick 16 in the reverse direction in which it was tightened.

Figure 19:
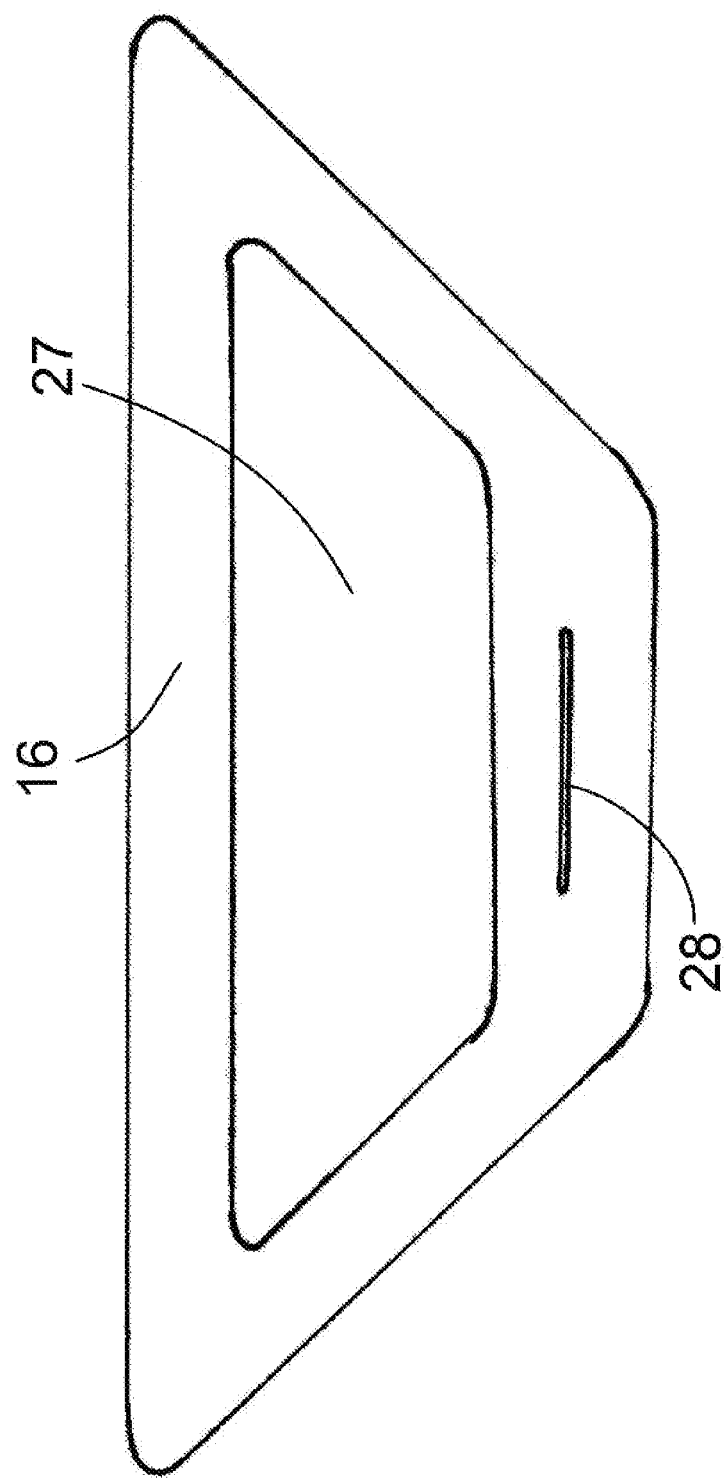
FIG. 19 is a side view of a windlass stick.

Referring to FIG. 19, windlass stick 16 is shown. Windlass stick 16 takes the form of a trapezoid with a trapezoidal hole 27 cut out of the center. Cutout 27 allows the windlass stick to be locked into carabiner clasp 17a or 17b to secure the windlass and hold the tension generated by turning the windlass stick 16. The third elongated member 14 passes through slot 28. Slot 28 is located in the narrow, bottom portion of the windlass stick 16 and is the central point where the helix of the third elongated member 14 forms when the windlass is tightened. The trapezoidal shape of windlass stick 16 has a wide, top portion allowing for a 'power grip' stance to be applied by the user. For example, the user may hold the wide top portion of windlass stick 16 in a tight fist which allows the user to apply more torque. The windlass stick 16 is made from a sufficiently rigid and strong material to handle the torques applied/necessary for this device to be effective. In an embodiment, the windlass stick is formed from metal, e.g., aluminum.

Figure 20:
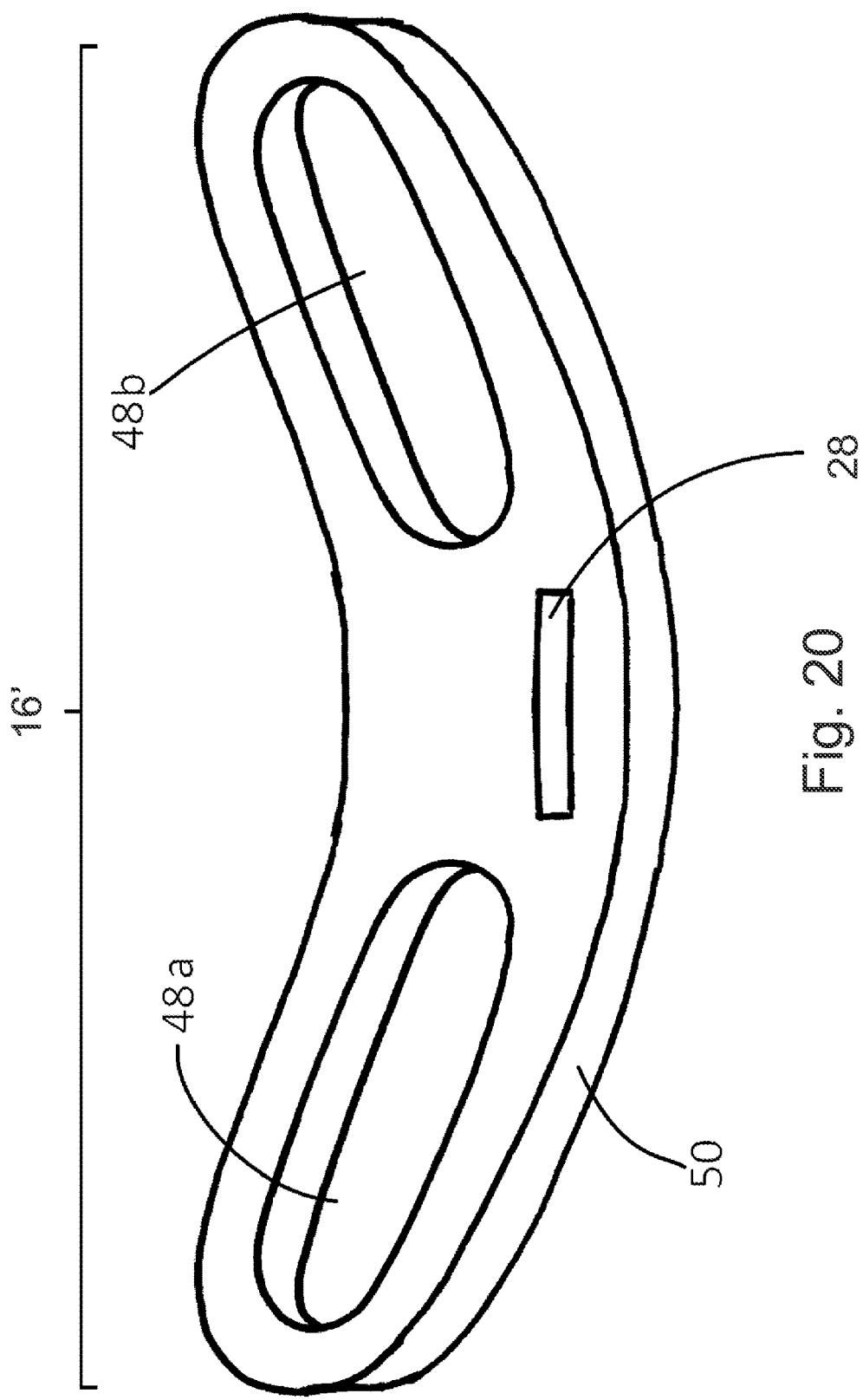
FIG. 20 is a perspective view of an alternative embodiment of a windlass stick.

Referring to FIG. 20, an alternative embodiment of a windlass stick is shown. Windlass stick 16' includes a slot 28 for receiving a windlass strap and securing cutouts 48a and 48b. Securing cutouts 48a, 48b are shaped and sized to mate effectively with a clasp or clasps. The lower curved edge 50 of windlass stick 16' is shaped to enable a rocking motion of the windlass stick 16'. This feature ensures clearance of clasps and any bulging fabric or tissue around the tourniquet 1 during tightening.

Alternative embodiments of tightening mechanisms capable of shortening an elongated member and providing additional compression can include ratcheting and/or lever combinations, gear drives, block-and-tackle pulley systems, or any combination thereof.

The first elongated member (cinch member 3), the second elongated member 13 and the third elongated member 14 can be made from continuous materials with sufficient compliance to conform about the surface of a curved object or limb. Such material may be webbing, cables, ropes, netting, elastic materials or any combination thereof.

Figure 21:
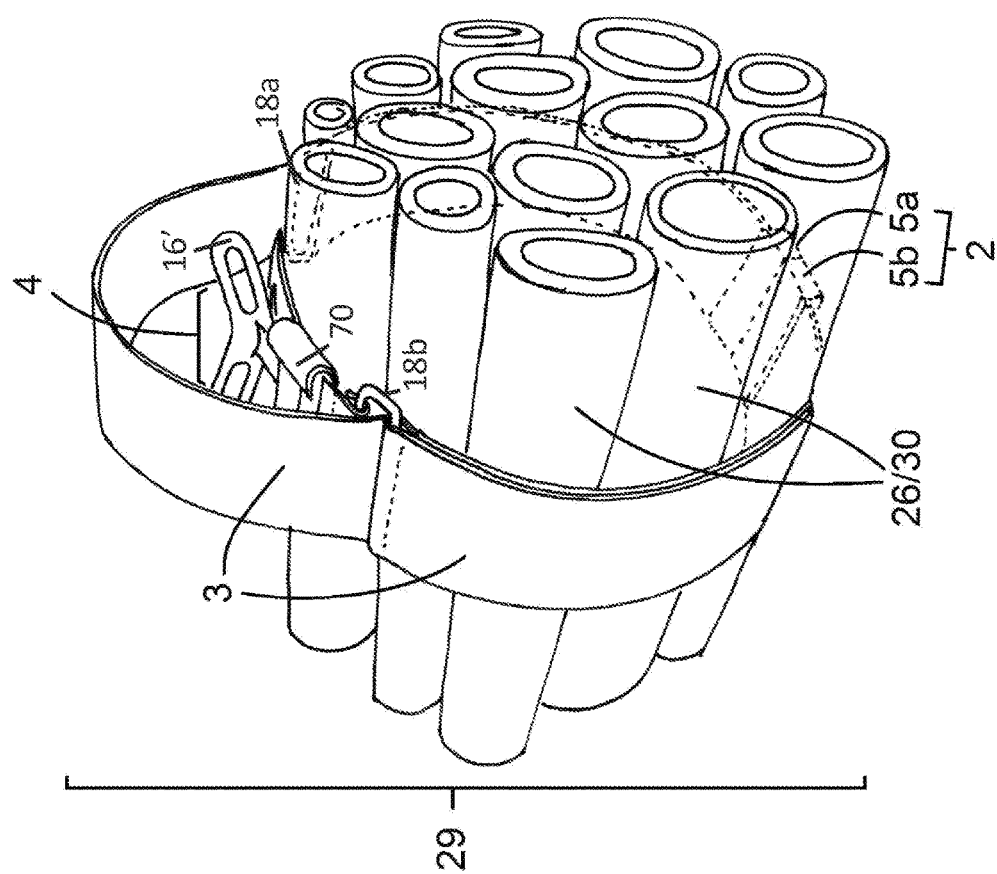
FIG. 21 is a perspective view of a compression device useful as a harness, tie, compression strap or handle and shown in cinched state around a plurality of objects, hollow pipes here.

Referring to FIG. 21, a compression device 29, which can be used as a harness, tie, or handle in accordance with embodiments of the present invention, is shown. The compression device 29 includes cinch member 3, tightening mechanism 4, guidance slides 18a and 18b, and first buckle assembly 2. As shown in FIG. 21, the compression device 29 can be used as a harness and a handle, such as but not limited to, to hold pipes 30 together and provide pipes 30 with a handle, or for any general object(s) 26. As shown in FIG. 21, the device 29 includes windlass stick 16' and clasp 70. Rotation of windlass stick 16' can further tighten cinch member 3 around pipes 30. Following tightening, a securing cutout of windlass stick 16' may receive clasp 70 to ensure that the tightening mechanism does not loosen. Instead of clasp 70, one or more carabiner clasps 17a, 17b (see, e.g., FIGS. 1 and 8 and associated description) can be provided on device 29 to secure the windlass stick.

Figure 22:
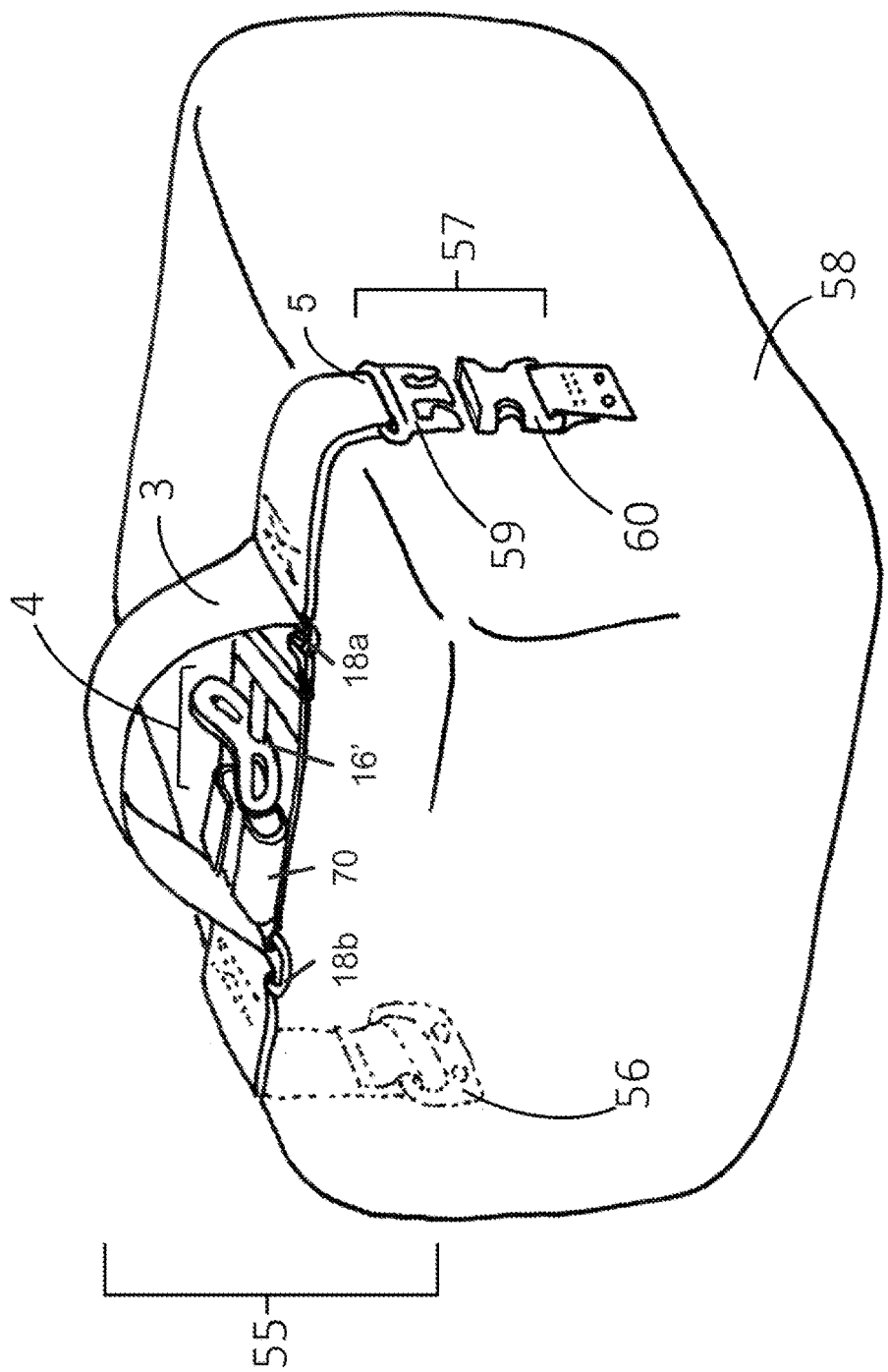
FIG. 22 is a perspective view of a compression device useful as a luggage compression strap shown in relaxed state around a partially compressible object.

Referring now to FIG. 22, a luggage compression device 55, which can be used as a compression strap in accordance with embodiments of the present invention, is shown. The luggage compression device 55 includes cinch member 3, the tightening mechanism 4, and guidance slides 18a and 18b. A first buckle 56 is attached to one side of bag 58, and a second buckle assembly 57 is attached to another (e.g., opposite) side of bag 58. As shown in FIG. 22, the luggage compression device 55 can be used as a compression strap to compress and reduce the size of bag 58.

Referring still to FIG. 22, the second buckle assembly 57 includes a male buckle 59 and a female buckle 60. The cinch member 3 passes through sliding buckle 5 of the male buckle 59. Sliding buckle 5 is similar to sliding buckles 5a, 5b described with reference to FIGS. 10-15. The female end 60 of the second buckle assembly 57 is attached to bag 58. The male end 59 and the female end 60 of the second buckle assembly 57 are interchangeable. Also shown in FIG. 22 are windlass stick 16' and clasp 70. Rotation of windlass stick 16' can further compress bag 58. Windlass stick 16' may then be secured by clasp 70 to ensure that the tightening mechanism is not loosened. Instead of clasp 70, one or more carabiner clasps 17a, 17b (see, e.g., FIGS. 1 and 8) can be provided on device 55 to secure the windlass stick.

Alternative embodiments of the present invention may omit tightening mechanism 4, as shown, for example, in FIG. 16, if the compression device is intended to be applied to objects for which further tightening after initial application is not required.

While this invention has been particularly shown and described with references to example embodiments thereof, it will be understood by those skilled in the art that various changes in form and details may be made therein without departing from the scope of the invention encompassed by the appended claims.

What is claimed is:

1. A compression device, comprising:
   a buckle assembly including a first buckle and a second buckle;
   a first guidance slide;
   a second guidance slide;
   a connecting member between the first and second guidance slides; and
   a strap having a first end and a second end, the first end anchored to the first guidance slide, the second end anchored to the second guidance slide,
   the strap passing from the first guidance slide through the first buckle, forming a first outer segment,
   the strap returning on an inside of the first outer segment and through the first guidance slide, forming a first inner segment,
   the strap passing on an outside of the connecting member,
   the strap passing through the second guidance slide and through the second buckle, forming a second inner segment,
   the strap returning on an outside of the second inner segment to the second guidance slide, forming a second outer segment,
   the buckle assembly, the inner segments, and connecting member forming a loop for placing about an object, an inner circumference of the loop being adjustable by pulling on a portion of the strap located along the outside of the connecting member and between the two guidance slides to tighten the loop around the object.

2. The compression device of claim 1, further comprising a tightening mechanism between the first and second guidance slides to further tighten the loop around the object.

3. The compression device of claim 2, wherein the tightening mechanism is a windlass that includes a windlass strap connected to the connecting member between the first and second guidance slides, and that further includes a windlass stick defining a slot through which the windlass strap passes.

4. The compression device of claim 3, wherein the windlass stick has a shape having a wide top portion for grasping and a narrow bottom portion having the slot through which the windlass strap passes.

5. The compression device of claim 4, wherein the windlass stick has a trapezoidal shape.

6. The compression device of claim 4, wherein the windlass stick includes one or more openings.

7. The compression device of claim 6, further comprising a locking mechanism to lock the windlass stick in place.

8. The compression device of claim 7, wherein the locking mechanism includes one or more carabiner clasps to engage an opening in the windlass stick.

9. The compression device of claim 1, wherein the strap is webbing.

10. The compression device of claim 1, further comprising a second buckle assembly to separate the strap into two parts.

11. The compression device of claim 10, wherein the second buckle assembly is connected in-line with the portion of the strap located along the outside of the connecting member and between the two guidance slides.

12. The compression device of claim 1, wherein the buckle assembly includes a popper assembly that releasingly connects the first and second buckles.

13. The compression device of claim 12, wherein the popper assembly includes at least one male popper riveted to a short flexible member and at least one female popper riveted to a second short flexible member, the flexible members each attached to the buckle assembly.

14. The compression device of claim 1, wherein each buckle includes a rigid projection configured to prevent rotation of the buckle relative to the buckle assembly.

15. The compression device of claim 1, wherein each buckle includes a single direction locking mechanism.

* * * * *